US011823802B2

(12) United States Patent
Mansfield et al.

(10) Patent No.: US 11,823,802 B2
(45) Date of Patent: Nov. 21, 2023

(54) SYSTEM AND METHOD TO RETROFIT A ROOM FOR VIRTUAL SITTING

(71) Applicant: Laux/Arnold, Incorporated, Fort Wayne, IN (US)

(72) Inventors: Michael O. Mansfield, Fort Wayne, IN (US); Christopher L. Rose, Fort Wayne, IN (US)

(73) Assignee: Laux/Arnold, Incorporated, Fort Wayne, IN (US)

( * ) Notice: Subject to any disclaimer, the term of this patent is extended or adjusted under 35 U.S.C. 154(b) by 517 days.

(21) Appl. No.: 17/176,112

(22) Filed: Feb. 15, 2021

(65) Prior Publication Data

US 2022/0262530 A1 Aug. 18, 2022

(51) Int. Cl.
*G16H 80/00* (2018.01)
*H04R 5/02* (2006.01)
(Continued)

(52) U.S. Cl.
CPC .......... *G16H 80/00* (2018.01); *F16M 13/027* (2013.01); *G06V 20/52* (2022.01);
(Continued)

(58) Field of Classification Search
CPC ........ H04N 23/50; H04N 23/51; H04N 23/52; H04N 23/54; H04N 23/55; H04N 23/56; H04N 23/57; H04N 23/60; H04N 23/61; H04N 23/611; H04N 23/65; H04N 23/651; H04N 7/183; H04R 5/02; H04R 1/025; H04R 1/028; H04R 2201/021;
(Continued)

(56) References Cited

U.S. PATENT DOCUMENTS 8,384,526 B2 * 2/2013 Schuman, Sr. ........ A61B 5/002
340/286.07
8,803,668 B2 8/2014 Schuman et al.
(Continued)

FOREIGN PATENT DOCUMENTS

EP 3 242 464 A1 8/2017

OTHER PUBLICATIONS

Avasys, The Emerging Solution to Patient Falls, 17 pages, 2014.

*Primary Examiner* — Twyler L Haskins
*Assistant Examiner* — Akshay Trehan
(74) *Attorney, Agent, or Firm* — McDonnell Boehnen Hulbert & Berghoff LLP

(57) ABSTRACT

An example system for monitoring an occupant of a room includes an enclosure, a speaker plate, a speaker, an infrared illuminator, a camera, and a power-over-Ethernet (PoE) splitter. The enclosure is mountable within an interior surface of the room. The speaker plate is removably positionable within the enclosure, and includes a speaker opening and an illuminator opening. The speaker is positioned within the speaker opening and mounted to the speaker plate. The infrared illuminator is positioned within the illuminator opening and mounted to the speaker plate. The PoE splitter is configured to: receive power and data over a first Ethernet cable, provide power to the speaker, the infrared illuminator, and the camera; and output the data to the camera over a second Ethernet cable. The camera is configured to send an audio signal to the speaker over an audio cable.

20 Claims, 5 Drawing Sheets

(51) Int. Cl.
| | |
|---|---|
| G06V 20/52 | (2022.01) |
| H04N 23/51 | (2023.01) |
| H04N 23/56 | (2023.01) |
| F16M 13/02 | (2006.01) |
| G08B 13/196 | (2006.01) |
| G16H 40/67 | (2018.01) |
| H04N 23/57 | (2023.01) |
| H04N 23/65 | (2023.01) |
| H04R 1/02 | (2006.01) |
| H04N 7/18 | (2006.01) |
| F16M 11/04 | (2006.01) |
| G06F 1/16 | (2006.01) |

(52) U.S. Cl.
CPC . *G08B 13/19632* (2013.01); *G08B 13/19636* (2013.01); *G16H 40/67* (2018.01); *H04N 7/183* (2013.01); *H04N 23/51* (2023.01); *H04N 23/56* (2023.01); *H04N 23/57* (2023.01); *H04N 23/65* (2023.01); *H04R 1/025* (2013.01); *H04R 5/02* (2013.01); *F16M 11/04* (2013.01); *G06F 1/1686* (2013.01); *G06F 1/1688* (2013.01); *H04R 1/028* (2013.01); *H04R 2201/021* (2013.01)

(58) Field of Classification Search
CPC ........ G16H 80/00; G16H 40/67; G06V 20/52; G03B 17/02; G03B 17/56; G03B 17/561; G03B 17/566; G03B 2217/00; G03B 2217/002; H05K 2201/10121; G08B 13/19617–19636; F16M 11/00; F16M 11/02; F16M 13/00–027; G06F 1/1686; G06F 1/1688
See application file for complete search history.

(56) References Cited

U.S. PATENT DOCUMENTS

| | | | |
|---|---|---|---|
| 9,235,979 | B2 | 1/2016 | Schuman, Sr. et al. |
| 9,411,934 | B2 | 8/2016 | Robinson et al. |
| 9,866,801 | B2 * | 1/2018 | Duffy .................... H04N 23/50 |
| 2006/0103636 | A1 * | 5/2006 | Parsons ................. F16M 11/24 |
| | | | 345/173 |
| 2016/0358435 | A1 * | 12/2016 | Lee ..................... G08B 13/1963 |
| 2018/0294982 | A1 * | 10/2018 | Boemi .................... H01R 13/52 |
| 2019/0323702 | A1 * | 10/2019 | Adejumo ............ F21V 33/0076 |
| 2020/0074825 | A1 * | 3/2020 | Martin ................... G05B 15/02 |
| 2022/0224805 | A1 * | 7/2022 | Gant .................... H04N 23/661 |

* cited by examiner

SYSTEM AND METHOD TO RETROFIT A ROOM FOR VIRTUAL SITTING

BACKGROUND

The use of technology to remotely observe and/or monitor healthcare patients is growing in popularity. Such remote observation and/or monitoring can be referred to as "virtual sitting". In a conventional virtual sitting system, a camera is provided in a patient's room, and a video feed from the camera is transmitted to an observation station at which a video feed from the patient's room is displayed. A healthcare professional can then observe and monitor the patient remotely via the video feed. When a healthcare professional observes the patient, an indicator (e.g., a light-emitting diode) on the camera can output an indication, which the patient can interpret to mean that a healthcare professional is using the camera to observe the patient. Some systems also provide audio equipment (e.g., a microphone and speaker) in the room and audio equipment at the observation station. A healthcare professional can then engage in one-way or two-way audio communication with the patient.

Moreover, when observation equipment is provided in multiple different patients' rooms, the healthcare professional can observe and monitor multiple patients simultaneously at the observation station. For instance, a display at the observation station can be configured to display multiple video feeds simultaneously.

There are multiple reasons that might warrant virtual sitting for a patient. As one example, the patient might have a highly-contagious virus. As another example, the patient might be at risk of falling and suffering a physical injury. As still another example, the patient might be suffering from a degenerative brain disease. Other examples are also possible. In some instances, the use of virtual sitting can reduce or eliminate the need to have a healthcare professional enter into a patient's room to temporarily observe a patient face-to-face.

SUMMARY

Example embodiments are described herein. In one example aspect, a system for monitoring an occupant of a room is described. The system includes an enclosure, a speaker plate, a speaker, an infrared illuminator, a camera, and a power-over-Ethernet (PoE) splitter. The enclosure is mountable within an interior surface of the room. The speaker plate is removably positionable within the enclosure, and includes a speaker opening and an illuminator opening. The speaker is positioned within the speaker opening and mounted to the speaker plate such that audio output by the speaker is directed toward a location of the occupant within the room. The infrared illuminator is positioned within the illuminator opening and mounted to the speaker plate such that light output by the infrared illuminator is directed toward the location of the occupant within the room. The PoE splitter is configured to: receive power and data over a first Ethernet cable, provide power to the speaker, the infrared illuminator, and the camera; and output the data to the camera over a second Ethernet cable. The camera is configured to send an audio signal to the speaker over an audio cable.

In another example aspect, a monitoring apparatus is described. The monitoring apparatus includes an enclosure, a speaker plate, a speaker, an infrared illuminator, and a PoE splitter. The enclosure is mountable within an interior surface of a room. The speaker plate is removably positionable within the enclosure, and includes a speaker opening and an illuminator opening. The speaker is positioned with the speaker opening and mounted to the speaker plate such that audio output by the speaker is directed toward a location of an occupant within the room. The infrared illuminator is positioned within the illuminator opening and mounted to the speaker plate such that light output by the infrared illuminator is directed toward the location of the occupant within the room. The PoE splitter is mounted to an interior side of the speaker plate. The PoE splitter includes a first Ethernet port for receiving power and data over a first Ethernet cable, a second Ethernet port for data communication with a camera, and a power port for outputting power to the speaker and the infrared illuminator. The speaker includes an audio port for receiving an audio signal from the camera over an audio cable.

In still another example aspect, a method to retrofit a room for virtual sitting is described. The method includes mounting an enclosure of a monitoring apparatus within an interior surface of the room. The monitoring apparatus includes a speaker plate that is removably positionable within the enclosure, a speaker mounted to the speaker plate, an infrared illuminator mounted to the speaker plate, and a PoE splitter mounted to the speaker plate. The method also includes coupling the PoE splitter to a PoE injector using a first Ethernet cable. In addition, the method includes coupling the PoE splitter to a camera using a second Ethernet cable. Further, the method includes coupling the speaker to the camera using an audio cable. And the method includes positioning the speaker plate within the enclosure.

These aspects, as well as other embodiments, aspects, advantages, and alternatives will become apparent to those of ordinary skill in the art by reading the following detailed description, with reference where appropriate to the accompanying drawings. Further, this summary and other descriptions and figures provided herein are intended to illustrate embodiments by way of example only and, as such, that numerous variations are possible. For instance, structural elements and process steps can be rearranged, combined, distributed, eliminated, or otherwise changed, while remaining within the scope of the embodiments as claimed.

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying figures, wherein:

DETAILED DESCRIPTION

Figure 1:
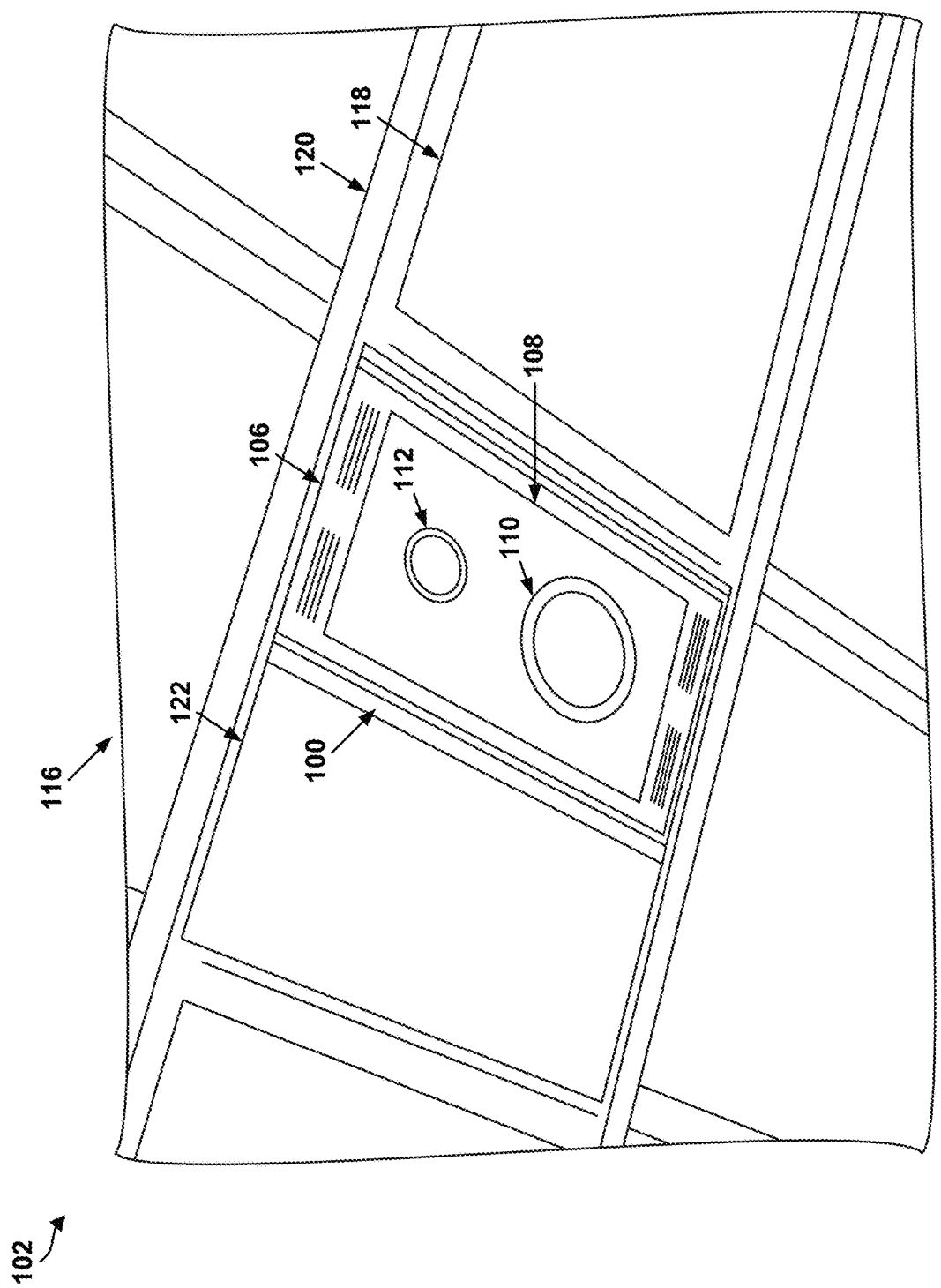
FIG. 1 shows an example monitoring apparatus, according to an example.

Disclosed examples will now be described more fully hereinafter with reference to the accompanying figures, in which some, but not all of the disclosed examples are shown.

Indeed, several different examples may be provided and should not be construed as limited to the examples set forth herein. Rather, these examples are provided so that this disclosure will be thorough and complete and will fully convey the scope of the disclosure to those skilled in the art.

Throughout this description, the articles "a" or "an" are used to introduce elements of the example embodiments. Any reference to "a" or "an" refers to "at least one," and any reference to "the" refers to "the at least one," unless otherwise specified, or unless the context clearly dictates otherwise. The intent of using the conjunction "or" within a described list of at least two terms is to indicate any of the listed terms or any combination of the listed terms.

The use of ordinal numbers such as "first", "second", "third", and so on is to distinguish respective elements rather than to denote a particular order of those elements. For purpose of this description, the terms "multiple" and "a plurality of" refer to "two or more" or "more than one."

Further, unless context suggests otherwise, the features illustrated in each of the figures may be used in combination with one another. Thus, the figures should be generally viewed as component aspects of one or more overall embodiments, with the understanding that not all illustrated features are necessary for each embodiment.

As noted above, virtual sitting systems are growing in popularity. Some conventional virtual sitting systems include mobile platforms to which a camera and audio equipment are mounted. These mobile platforms are sometimes powered by rechargeable battery packs. However, such battery backs only store a limited amount of power and are recharged once the power is depleted. Other mobile platforms overcome this deficiency through the use of power cords that can be connected to electrical wall outlets. However, such power cords can limit the mobility of the virtual system and are a trip hazard.

Other virtual sitting systems are stationary or fixed systems in which cameras and audio equipment are mounted to structures of a room and hard-wired to 120 volts alternating current (VAC) power. The use of 120 VAC power, however, can create additional complications when retrofitting a room to include a virtual sitting system. For instance, due to the need to install new electrical components (e.g., circuit breakers, conductors, etc.), an installer of the virtual sitting system might have to obtain an electrical hot work permit before installing the system. The process of obtaining the electrical hot work permit can add delays and costs to the installation. Moreover, such an installation might require the services of an electrician, which can further increase the cost of the installation.

Described herein are virtual sitting systems that address these and potentially other issues. An example system includes a camera, an enclosure that is mountable within an interior surface of a room, and a speaker plate that is removably positionable within the enclosure. The speaker plate, in turn, includes a speaker opening and an illuminator opening that support a speaker and an infrared illuminator, respectively.

Further, a PoE splitter is mounted to an interior side of the speaker plate. The PoE splitter is configured to receive power over an Ethernet cable, and to provide power to other electrical components of the system, namely, the speaker, the infrared illuminator, and the camera. Advantageously, the speaker, the infrared illuminator, and the camera are operable using the power provided by the PoE splitter and without requiring another power source. Because these components of the system are all powered by power that the PoE splitter extracts from an Ethernet cable rather than 120 VAC, the system eliminates the need to obtain an electrical hot work permit and utilize services of an electrician when installing the system in a room. As such, the system is intelligently-tailored for use in retrofitting an existing room to include virtual sitting capabilities.

Another benefit of powering the system by way of PoE is that the system can easily be tied into a back-up electrical system for a building. For instance, a PoE injector that provides power to the PoE Splitter over an Ethernet cable can be coupled to a back-up electrical system of the building that operates when a primary power source for the building is comprised. As an example, the PoE injector can be coupled to a battery backup system along with other networking hardware for the building. In this manner, the PoE injector, and therefore the PoE splitter, can continue to provide power to the system in the event that the primary power source for the building is comprised.

In some instances, the enclosure is sized for positioning the enclosure within a dropped ceiling. As an example, the dropped ceiling can include ceiling tiles supported by a ceiling time framework, as is common in many healthcare buildings. Further, the enclosure can be sized for positioning the enclosure within a single grid cell of the ceiling time framework. With this approach, electrical cables for the system, such as an Ethernet cable that provides power and data to the system, can be easily routed to the enclosure above the ceiling tile framework.

Additional examples of the described systems, and associated methods, are also described hereinafter with reference to the accompanying figures.

Figure 2B:
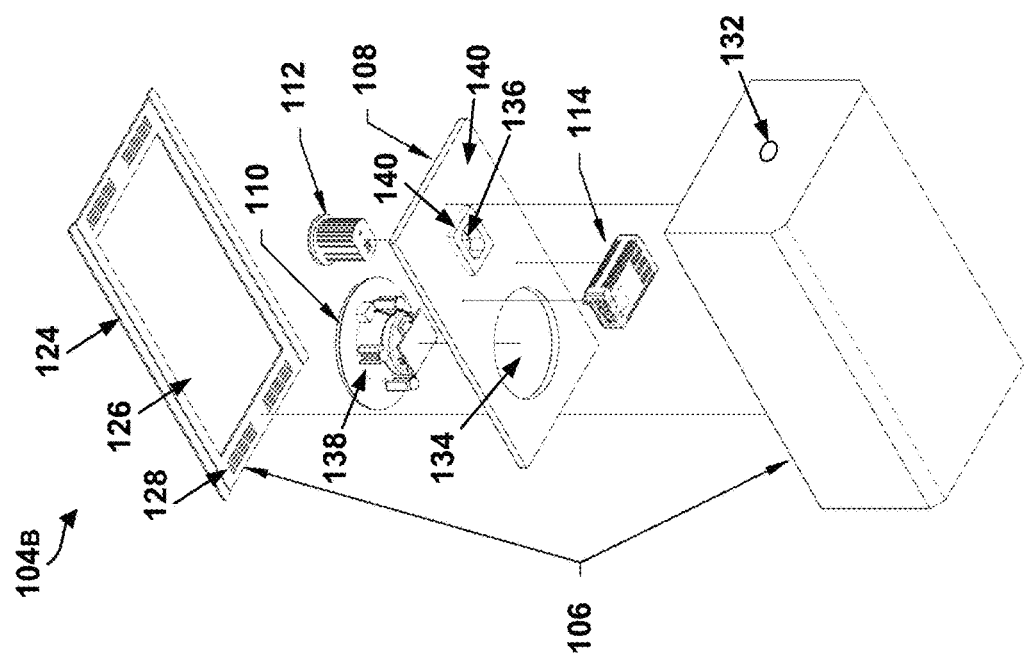
FIGS. 2A and 2B show exploded views of the monitoring apparatus of FIG. 2.
Figure 2A:
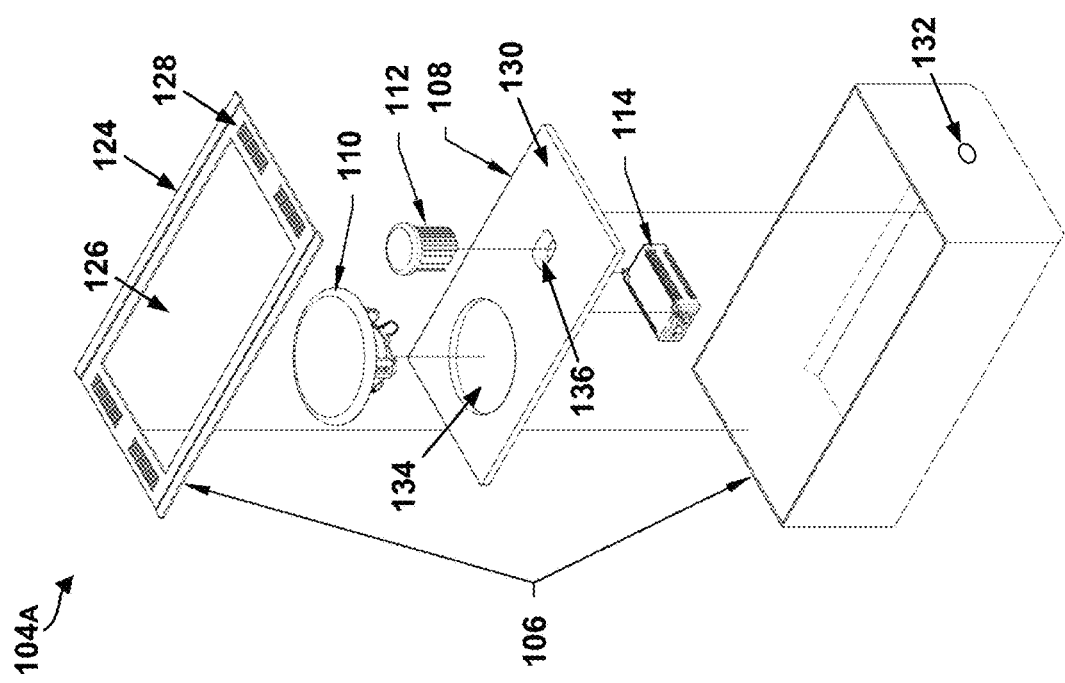

Referring now to the figures, FIGS. 1, 2A, and 2B show an example monitoring apparatus 100. In particular, FIG. 1 illustrates a front view of monitoring apparatus 100; FIG. 2A illustrates a first exploded view of monitoring apparatus 100; and FIG. 2B illustrates a second exploded view of monitoring apparatus 100. In line with the discussion above, monitoring apparatus 200 can be used for monitoring an occupant of a room. As shown in FIGS. 1, 2A, and 2B, monitoring apparatus 100 includes an enclosure 106, a speaker plate 108, a speaker 110, an infrared illuminator 112, and a PoE splitter 114.

Enclosure 106 is mountable within an interior surface of a room. By way of example, enclosure 106 can be mountable within a ceiling of a room. For instance, as shown in FIG. 1, enclosure 106 can take the form of a storage box that is mountable within a dropped ceiling 116 that includes ceiling tiles 118 supported by a ceiling tile framework 120. Optionally, enclosure 106 can be sized for positioning enclosure within a single grid cell 122 of ceiling tile framework 120. As one example, each ceiling tile 118 can be a two-foot by two-foot square, and enclosure 106 can have a width of approximately one foot and a length of approximately two feet, such that enclosure occupies one half of single grid cell 122. Alternatively, enclosure can have a width of approximately two feet and a length of approximately two feet.

Enclosure 106 can be installed using wires or cables that are attached to the frame of the room (e.g., using anchors) at a first end and attached to enclosure 106 at a second end. In this manner, the frame of the room that is located above the dropped ceiling can support the weight of enclosure 106. In other examples, enclosure 106 can be mounted within a wall of a room (not shown).

Further, enclosure 106 includes a front surface 124 having a speaker-plate opening 126 and vents 128. Speaker plate 108 is insertable within speaker-plate opening 126. For instance, during installation of monitoring apparatus 100, speaker plate 108 can be inserted within speaker-plate opening 126 by turning speaker plate 108 at an angle, inserting speaker plate 108 through speaker-plate opening 126, and then adjusting speaker plate 108 such that front surface 124 of enclosure 106 contacts speaker plate 108 along a perimeter of an exterior side 130 of speaker plate 108. As such, exterior side 130 of speaker plate 108 can be flush-mounted with a ceiling or wall of a room.

For a configuration in which enclosure 106 is mounted within a ceiling, the weight of speaker plate 108 can hold speaker plate 108 in position within enclosure 106. For a configuration in which enclosure 106 is mounted within a wall, speaker plate 108 can be affixed to enclosure 106 using a suitable attachment mechanism, such as magnets, fasteners, Velcro, etc. Vents 128 allow air to circulate through enclosure 106, thereby cooling components within enclosure 106.

Enclosure 106 also includes one or more wire openings 132 that allow cables to enter enclosure 106 and exit enclosure 106. For instance, one or more sides or a bottom surface of enclosure 106 can include wire knockouts that are removable for creating wire openings within the sides or bottom surface of enclosure. During installation, a first Ethernet cable that provides power and data to PoE splitter 114 can be inserted within a wire opening of enclosure 106. Further, a second Ethernet cable that connects PoE splitter 114 to a camera can be inserted within a wire opening wire opening of enclosure 106. Still further, an audio cable that connects the camera and speaker 110 can be inserted within a wire opening of enclosure 106.

Speaker plate 108 includes a speaker opening 134 and an illuminator opening 136. Speaker opening 134 is configured for receiving speaker 110. Speaker 110 can take the form of an amplified speaker that outputs audio. Further, speaker 110 includes mounting tabs 138 that are movable for securing speaker 110 to speaker plate 108 after speaker 110 is partially inserted through speaker opening 134. In some examples, speaker opening 134 is slightly smaller than a diameter of a grille of speaker 110, such that speaker 110 can be flush-mounted to exterior side 130 of speaker plate 108. By mounting speaker 110 within speaker opening 134 and appropriately locating enclosure 106 within a room, audio output by speaker can be directed toward a location of an occupant within the room.

Illuminator opening 136 is configured for receiving infrared illuminator 112. Infrared illuminator 112 can be a low-profile, illuminator that outputs infrared light over a wide coverage area (e.g., 140 degrees, 150 degrees, 160 degrees, etc.). In some examples, illuminator opening is slightly smaller than a diameter of a lens of infrared illuminator 112, such that the lens of infrared illuminator 112 can be flush-mounted to exterior side 130 of speaker plate 108.

Further, various attachment mechanisms can be used to secure infrared illuminator 112 within illuminator opening 136 after infrared illuminator 112 is partially inserted within illuminator opening 136. As one example, a metal clip can be clipped around a body of infrared illuminator 112 to secure a position of infrared illuminator 112 within speaker plate 108. The metal clip (not shown) can effectively increase a diameter of infrared illuminator 112 to a size that is larger than a diameter of illuminator opening 136, such that infrared illuminator cannot slide out of illuminator opening 136. As another example, set screws (not shown) provided within a raised portion 140 that surrounds illuminator opening 136 on an interior side 140 of speaker plate can be tighten to secure infrared illuminator 112 within illuminator opening 136.

By mounting infrared illuminator 112 within illuminator opening 136 and appropriately locating enclosure 106 within a room, light output by infrared illuminator 112 can be directed toward a location of an occupant within the room. The light output by infrared illuminator 112 can allow a camera to obtain images of the occupant in dark or low-light conditions (e.g., when lights are off in the room).

PoE splitter 114 is mounted to interior side 140 of speaker plate 108. For instance, PoE splitter 114 can be attached to interior side 140 using fasteners. Further, PoE splitter 114 can include a first Ethernet port for receiving power and data over an input Ethernet cable, a second Ethernet port for data communication with another device over an output Ethernet cable, and a power port for outputting power to one or more other devices. For instance, PoE splitter can include a 60-watt PoE splitter that receives power and data over a first Ethernet Cable, outputs about 4.5 amps at 12 Volts by way of the power port, and outputs the data over a second Ethernet cable. PoE splitter 114 can also receive data via the second Ethernet cable and output the data over the first Ethernet cable. PoE splitter 114 can be powered from a PoE injector that outputs power over the input Ethernet cable from a remote location that is outside of the room.

In line with the discussion above, the power output by PoE splitter 114 can be used to power speaker 110 and infrared illuminator 112. In addition, the power output by PoE splitter 114 can be used to power another component, such as a camera. Advantageously, PoE splitter 114 can serve as the only power source for those components. Put another way, speaker 110 and infrared illuminator 112 can be operable using only the power provided by PoE splitter 114 and without requiring another power source.

Figure 3:
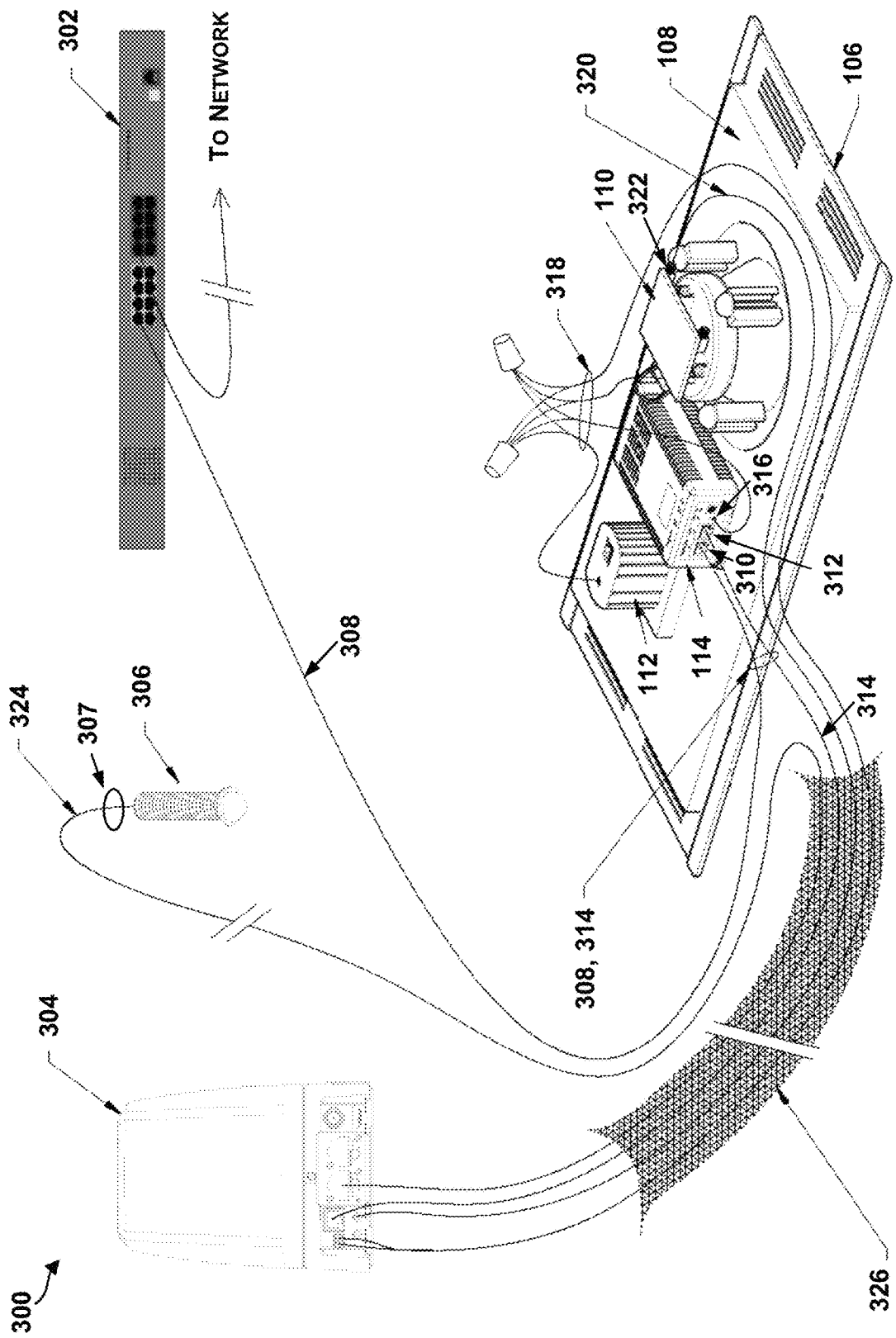
FIG. 3 is a diagram of an example system for monitoring an occupant of a room, according to an example.

FIG. 3 is a diagram of an example system 300 for monitoring an occupant of a room, according to an example. System 300 includes monitoring apparatus 100, a PoE injector 302, a camera 304, and a microphone 306. As shown in FIG. 3, monitoring apparatus 100 includes enclosure 106, speaker plate 108, speaker 110, infrared illuminator 112, and PoE splitter 114. For ease of explanation, a portion of enclosure 106 has been removed.

PoE injector 302 outputs power over a first Ethernet cable 308. PoE injector 302 can include a midspan or a PoE switch, for instance. PoE splitter 114 includes a first Ethernet port 310 for receiving power and data over first Ethernet cable 308. In addition, PoE splitter 114 includes a second Ethernet port 312 for data communication with camera 304 over a second Ethernet cable 314. Further, PoE splitter 114 includes a power port 316 for outputting power to speaker 110, infrared illuminator 112, and camera 304. Power output from power port 316 is distributed to speaker 110, infrared illuminator 112, and camera 304 using electrical wires 318.

Camera 304 can include a network camera that is configured to obtain images of a room. Camera 304 can transmit the images to a network by way of second Ethernet cable 314, PoE splitter 114, first Ethernet cable 308, and PoE injector 302. In addition, an operator can use a computing device coupled to the network to send control commands to camera 304 by way of PoE injector 302, first Ethernet cable 308, PoE splitter 114, and second Ethernet cable 314. The control commands can control functions of camera 304 such as rotate, pan, tilt, and/or zoom, for instance. The control commands can also be utilized to instruct camera 304 when to start and stop obtaining images.

Further, camera 304 can be configured to send an audio signal to speaker 110 using a first audio cable 320. First audio cable 320 can be connected to an audio port 322 of speaker 110. First audio cable 320 can include a 3.5 mm audio cable, for instance. As such, an operator can use a computing device coupled to the network to provide audio data to camera 304, which camera 304, in turn, can relay to speaker 110 as an audio signal for output by speaker 110. With such a configuration, the operator can speak to an occupant of the room or cause speaker 110 to output a pre-recorded voice command.

Microphone 306 is configured to convert sounds within the room to audio signals. Microphone 306 can take various forms, depending on the desired implementation. As one example, microphone 306 can include a boundary microphone that can be positioned near or flush-mounted with a surface, such as a table or a wall. Microphone can be mounted to a structure using a lock ring 307. For instance, lock ring 307 can be threaded onto microphone 306 after microphone 306 is inserted through a hole in a ceiling or a wall. Microphone 306 is connected to camera 304 using a second audio cable 324. Second audio cable 324 can include an external line return (XLR) cable, for instance. The audio signal obtained by microphone 306 can be provided to camera via second audio cable 324. Camera 304, in turn, can then relay the audio signal to a computing device coupled to the network. As such, an operator can use the computing device to hear the occupant in the room.

Portions of second Ethernet cable 314, electrical wires 318, first audio cable 320, and second audio cable 324 can be provided within a wire loom 326. The use of wire loom 326 can help to organize and protect second Ethernet cable 314, electrical wires 318, first audio cable 320, and second audio cable 324.

Figure 4:
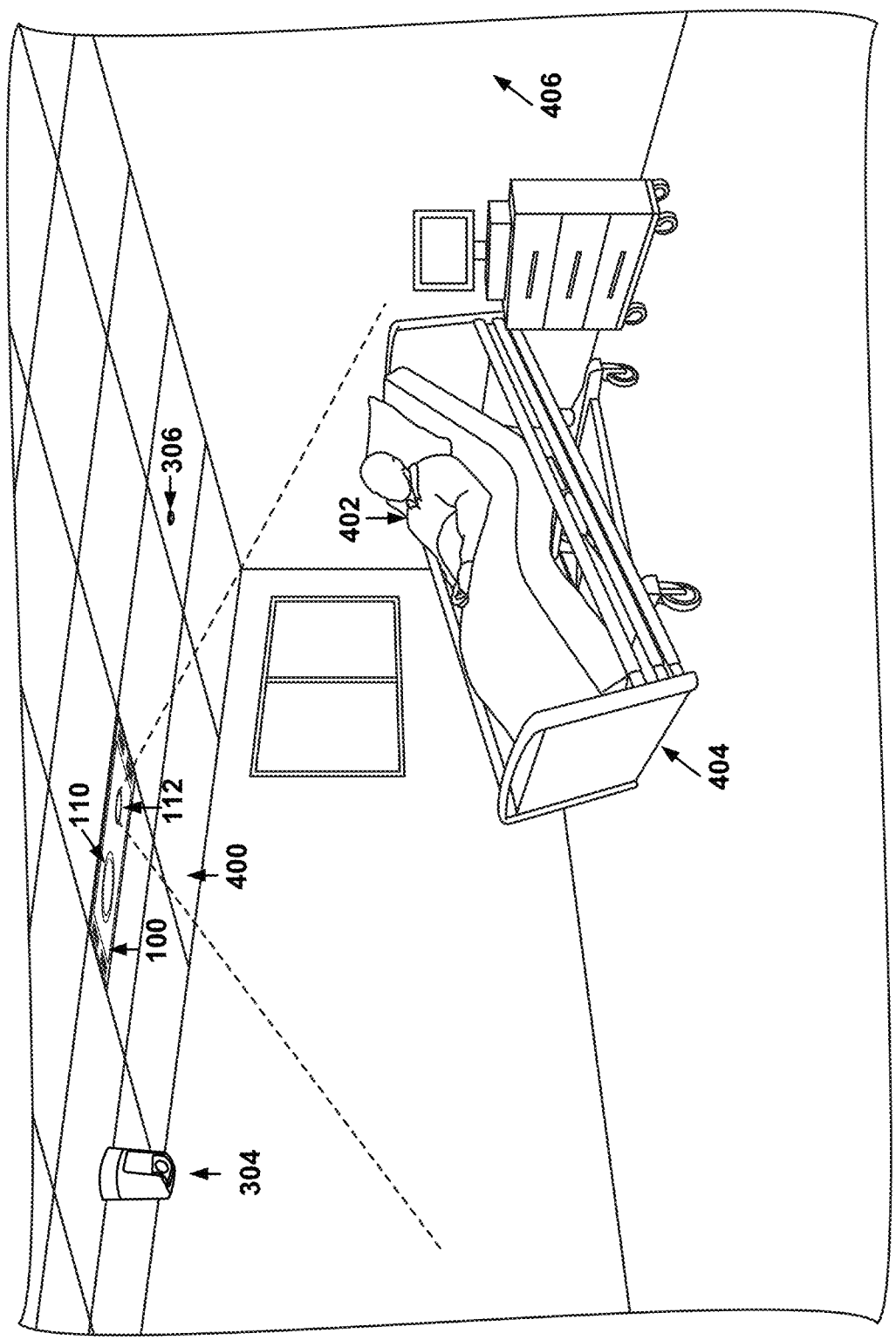
FIG. 4 shows an example installation of the system of FIG. 3, according to an example.

FIG. 4 shows an example installation of the system 300 of FIG. 3, according to an example. As shown in FIG. 4, monitoring apparatus 100 is mounted within a ceiling 400 of room. With this location, audio output by speaker 110 is directed toward a location of an occupant 402. Similarly, light output by infrared illuminator 112 is directed toward the location of occupant 402.

Further, camera 304 is mounted to ceiling 400, such that camera 304 can obtain images of occupant 402. With this arrangement, second Ethernet cable 314, electrical wires 318, first audio cable 320, and second audio cable 324 can be easily routed from monitoring apparatus 100 to camera 304 above the ceiling tiles of the dropped ceiling.

Still further, microphone 306 is also mounted to ceiling 400 of the room above a location of occupant 402. With this arrangement, second audio cable 324 can be routed from camera 304 to microphone 306 above the ceiling tiles of the dropped ceiling. With the installation shown in FIG. 4, microphone 306 is offset from mounting apparatus 100. In particular, mounting apparatus 100 is mounted above a foot of bed 406, and microphone 306 is mounted above a head of bed 404. This arrangement creates a physical separation between microphone 306 and speaker 110, thereby eliminating feedback. In other examples, microphone 306 can be mounted to a wall 406 of the room.

In line with the discussion above, due to the ease of installing and connecting the components of system 300, system 300 is readily applicable for use in retrofitting an existing room to include virtual sitting capabilities. Further, because the components of system 300 can all be powered by power that PoE splitter 114 extracts from an Ethernet cable, system 300 can be installed without having to obtain an electrical hot work permit and utilize services of an electrician.

Figure 5:
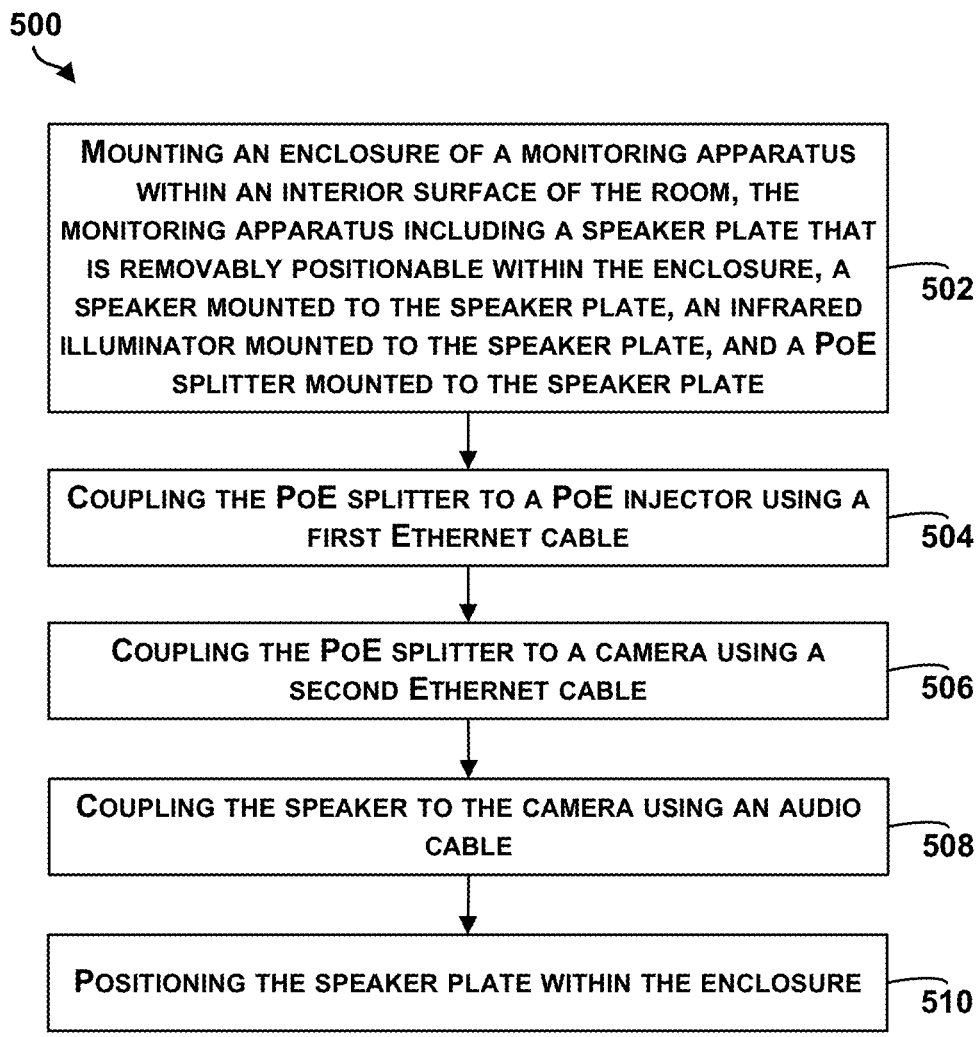
FIG. 5 shows a flowchart of a method, according to an example.

FIG. 5 shows a flowchart of a method 500, according to an example. Method 500 can be carried out to retrofit a room for virtual sitting. Alternatively, method 500 can be carried out to configure a room for virtual sitting during new construction.

Method 500 can include one or more operations, functions, or actions as illustrated by one or more of blocks 502-510. Although these blocks are illustrated in a sequential order, these blocks may also be performed in parallel, and/or in a different order than those described herein. Also, the various blocks may be combined into fewer blocks, divided into additional blocks, and/or removed based upon the desired implementation.

As shown in FIG. 5, at block 502, method 500 includes mounting an enclosure of a monitoring apparatus within an interior surface of the room. The monitoring apparatus includes a speaker plate this removably positionable within the enclosure, a speaker mounted to the speaker plate, an infrared illuminator mounted to the speaker plate, and a PoE splitter mounted to the speaker plate. For instance, the monitoring apparatus can be the monitoring apparatus 100 of FIGS. 1, 2A, and 2B, or any of the monitoring apparatuses contemplated herein.

In one example, mounting the enclosure within the interior surface of the room includes mounting the enclosure within a ceiling of the room. For instance, the ceiling can be a dropped ceiling, and mounting the enclosure can involve: removing a ceiling tile, inserting the enclosure into the ceiling through the opening left by the ceiling tile, and suspending the enclosure from a frame of the room using wires or cables that are anchored to the frame of the room.

Alternatively, mounting the enclosure within the interior surface of the room includes mounting the enclosure within a wall of the room. With this approach, a portion of the wall can be cut-out to create a space for the enclosure, and the enclosure can be inserted into the space in the wall. The enclosure can then be secured to the wall. For instance, the enclosure can be fastened to one or more studs in the wall.

At block 504, method 500 includes coupling the PoE splitter to a PoE injector using a first Ethernet cable. For instance, a first end of the first Ethernet cable can be plugged into a port of the PoE injector, and a second end of the first Ethernet cable can be plugged into a port of the PoE splitter. In some examples, the PoE injector can be located in another room, such as a server room. Accordingly, coupling the PoE splitter to the PoE injector can involve pulling or fishing the first Ethernet cable from a location of the PoE injector to the room.

At block 506, method 500 includes coupling the PoE splitter to a camera using a second Ethernet cable. Coupling the PoE splitter to the camera can involve plugging a first end of the second Ethernet cable into a port of the PoE splitter and plugging a second end of the second Ethernet cable into a port of the camera. In some instances, the second Ethernet cable can be routed between the camera and the PoE splitter in a manner that hides the second Ethernet cable from view. For instance, the second Ethernet cable can be routed to the camera above ceiling tiles of a dropped ceiling.

At block 508, method 500 includes coupling the speaker to the camera using an audio cable. Coupling the speaker to the camera can involve plugging a first end of the audio cable into a port of the camera and plugging a second end of the audio cable into a port of the speaker.

And at block 510, method 500 includes positioning the speaker plate within the enclosure. Positioning the speaker plate within the enclosure can involve rotating the speaker plate at an angle, inserting the speaker plate through an opening of a front surface of the enclosure, and adjusting the speaker plate such that the front surface of the enclosure contacts the speaker plate along a perimeter of an exterior side of the speaker plate.

In some examples, method 500 can also include coupling the speaker and the infrared illuminator to a power port of the PoE splitter. The speaker and the infrared illuminator can be coupled to the power port using electrical wires (e.g., 18/2 stranded wire)

The description of the different advantageous arrangements has been presented for purposes of illustration and description, and is not intended to be exhaustive or limited to the examples in the form disclosed. After reviewing and understanding the foregoing disclosure, many modifications and variations will be apparent to those of ordinary skill in the art. Further, different examples may provide different advantages as compared to other examples. The example or examples selected are chosen and described in order to best explain the principles, the practical application, and to enable others of ordinary skill in the art to understand the disclosure for various examples with various modifications as are suited to the particular use contemplated.

What is claimed is:

1. A system for monitoring an occupant of a room, the system comprising:
    an enclosure that is mountable within an interior surface of the room;
    a speaker plate that is removably positionable within the enclosure, the speaker plate comprising a speaker opening and an illuminator opening;
    a speaker positioned within the speaker opening and mounted to the speaker plate such that audio output by the speaker is directed toward a location of the occupant within the room;
    an infrared illuminator positioned within the illuminator opening and mounted to the speaker plate such that light output by the infrared illuminator is directed toward the location of the occupant within the room;
    a camera; and
    a power-over-Ethernet (PoE) splitter mounted to an interior side of the speaker plate,
    wherein the PoE splitter is configured to:
        receive power and data over a first Ethernet cable,
        provide power to the speaker, the infrared illuminator, and the camera, and
        output the data to the camera over a second Ethernet cable, and
    wherein the camera is configured to send an audio signal to the speaker over an audio cable.

2. The system of claim 1, further comprising a PoE injector configured to output power over the first Ethernet cable from a remote location that is outside of the room.

3. The system of claim 1, wherein the speaker, the infrared illuminator, and the camera are operable using the power provided by the PoE splitter and without requiring another power source.

4. The system of claim 1, further comprising a microphone that is coupled to the camera via another audio cable.

5. The system of claim 1, wherein:
    the speaker is flush-mounted to an exterior side of the speaker plate, and
    the infrared illuminator is flush-mounted to the exterior side of the speaker plate.

6. The system of claim 5, wherein the exterior side of the speaker plate is flush-mounted with the interior surface of the room.

7. The system of claim 6, wherein the interior surface of the room is a ceiling of the room.

8. The system of claim 7, wherein:
    the ceiling is a dropped ceiling comprising ceiling tiles supported by a ceiling tile framework, and
    the enclosure is sized for positioning the enclosure above the ceiling tile framework within a single grid cell of the ceiling tile framework.

9. The system of claim 6, wherein the interior surface of the room is a wall of the room.

10. The system of claim 1, wherein:
    the enclosure comprises a front surface having a speaker-plate opening, and
    the speaker plate is insertable within the speaker-plate opening.

11. The system of claim 10, wherein the front surface is configured to contact the speaker plate along a perimeter of an exterior side of the speaker plate when the speaker plate is positioned within the enclosure.

12. A monitoring apparatus comprising:
    an enclosure that is mountable within an interior surface of a room;
    a speaker plate that is removably positionable within the enclosure, the speaker plate comprising a speaker opening and an illuminator opening;
    a speaker positioned within the speaker opening and mounted to the speaker plate such that audio output by the speaker is directed toward a location of an occupant within the room;
    an infrared illuminator positioned within the illuminator opening and mounted to the speaker plate such that light output by the infrared illuminator is directed toward the location of the occupant within the room; and
    a power-over-Ethernet (PoE) splitter mounted to an interior side of the speaker plate, the PoE splitter comprising a first Ethernet port for receiving power and data over a first Ethernet cable, a second Ethernet port for data communication with a camera, and a power port for outputting power to the speaker and the infrared illuminator,
    wherein the speaker comprises an audio port for receiving an audio signal from the camera over an audio cable.

13. The monitoring apparatus of claim 12, wherein the speaker and the infrared illuminator are operable using the power output by the PoE splitter and without requiring another power source.

14. The monitoring apparatus of claim 12, wherein:
    the speaker is flush-mounted to an exterior side of the speaker plate, and
    the infrared illuminator is flush-mounted to the exterior side of the speaker plate.

15. The monitoring apparatus of claim 14, wherein the interior surface of the room is a ceiling of the room.

16. The monitoring apparatus of claim 14, wherein the interior surface of the room is a wall of the room.

17. The monitoring apparatus of claim 12, wherein:
    the enclosure comprises a front surface having a speaker-plate opening,
    the speaker plate is insertable within the speaker-plate opening, and
    the front surface is configured to contact the speaker plate along a perimeter of an exterior side of the speaker plate when the speaker plate is positioned within the enclosure.

18. A method to retrofit a room for virtual sitting, the method comprising:

mounting an enclosure of a monitoring apparatus within an interior surface of the room, the monitoring apparatus comprising:
  a speaker plate that is removably positionable within the enclosure,
  a speaker mounted to the speaker plate,
  an infrared illuminator mounted to the speaker plate, and
  a power-over-Ethernet (PoE) splitter mounted to the speaker plate;
coupling the PoE splitter to a PoE injector using a first Ethernet cable;
coupling the PoE splitter to a camera using a second Ethernet cable;
coupling the speaker to the camera using an audio cable; and
positioning the speaker plate within the enclosure.

19. The method of claim 18, further comprising:
coupling the speaker and the infrared illuminator to a power port of the PoE splitter.

20. The method of claim 18, wherein:
the interior surface of the room is a dropped ceiling comprising ceiling tiles supported by a ceiling tile framework, and
mounting the enclosure of the monitoring apparatus within the interior surface of the room comprises inserting the enclosure into the dropped ceiling through a single grid cell of the ceiling tile framework.

* * * * *